United States Patent
Habier

(10) Patent No.: US 12,272,429 B2
(45) Date of Patent: Apr. 8, 2025

(54) MOLECULAR BREEDING METHODS

(71) Applicant: PIONEER HI-BRED INTERNATIONAL, INC., Johnston, IA (US)

(72) Inventor: David Habier, Johnston, IA (US)

(73) Assignee: PIONEER HI-BRED INTERNATIONAL, INC., Johnston, IA (US)

( * ) Notice: Subject to any disclaimer, the term of this patent is extended or adjusted under 35 U.S.C. 154(b) by 711 days.

(21) Appl. No.: 15/108,425

(22) PCT Filed: Dec. 22, 2014

(86) PCT No.: PCT/US2014/071889
§ 371 (c)(1),
(2) Date: Jun. 27, 2016

(87) PCT Pub. No.: WO2015/100236
PCT Pub. Date: Jul. 2, 2015

(65) Prior Publication Data
US 2016/0321396 A1    Nov. 3, 2016

Related U.S. Application Data

(60) Provisional application No. 61/921,216, filed on Dec. 27, 2013.

(51) Int. Cl.
*G16B 20/00* (2019.01)
*C12Q 1/6888* (2018.01)
*C12Q 1/6895* (2018.01)

(52) U.S. Cl.
CPC ........... *G16B 20/00* (2019.02); *C12Q 1/6888* (2013.01); *C12Q 1/6895* (2013.01); *C12Q 2600/124* (2013.01); *C12Q 2600/13* (2013.01); *C12Q 2600/156* (2013.01)

(58) Field of Classification Search
None
See application file for complete search history.

(56) References Cited

U.S. PATENT DOCUMENTS

2012/0151625 A1    6/2012    Guo et al.

FOREIGN PATENT DOCUMENTS

WO    2008/025093 A1    3/2008

OTHER PUBLICATIONS

Jannink et al., (Briefings in Functional Genomics. Feb. 15, 2010;9(2):166-177). (Year: 2010).*
Hayes, B. J., Bowman, P. J., Chamberlain, A. J. & Goddard, M. E. Invited review: Genomic selection in dairy cattle: Progress and challenges. Journal of Dairy Science 92, 433-443 (2009).*
Lorenz, A. J. et al. Genomic Selection in Plant Breeding: Knowledge and Prospects. Advances in Agronomy 110, 77-123 (2011).*
Yu, B. & Yuan, B. A dynamic selection algorithm for globally optimal subsets. Engineering Applications of Artificial Intelligence 5, 457-462 (1992).*
Rex Bernardo et al., Prospects for Genomewide Selection for Quantitative Traits in Maize, Crop Science, May-Jun. 2007, pp. 1082-1090, vol. 47.
David Habier et al., Genomic BLUP Decoded: A Look into the Black Box of Genomic Prediction, Genetics, Jul. 2013, pp. 597-607, vol. 194.
Mark A. Hall et al., Benchmarking Attribute Selection Techniques for Discrete Class Data Mining, IEEE Transactions on Knowledge and Data Engineering, Nov./Dec. 2003, pp. 1437-1447, vol. 15, No. 6.
Jean-Luc Jannink et al., Genomic selection in plant breeding: from theory to practice, 2010, Briefings in Functional Genomics, pp. 166-177, vol. 9, No. 2.
Robenzon E. Lorenzana et al., Accuracy of genotypic value predictions for marker-based selection in biparental plant populations, Theor Appl Genet, 2009, pp. 151-161, vol. 120.
T. H. E. Meuwissen et al., Prediction of Total Genetic Value Using Genome-Wide Dense Marker Maps, Genetics, Apr. 2001, pp. 1819-1829, vol. 157.
International Search Report—PCT/US2014/071889—mailed Apr. 16, 2015.
Heng-De L., et al., "Genome Selection and its Application," Heritage [Y] 1-9, 2011, vol. 11, No. 13, pp. 1308-1316. English language copy from machine translation.
International Preliminary Report on Patentability for International Application No. PCT/US2014/071889, mailed Jul. 7, 2016, 9 Pages.

* cited by examiner

*Primary Examiner* — Soren Harward

(57) ABSTRACT

Methods to improve the selection of breeding individuals as part of a breeding program are provided in which optimized estimation data sets are constructed by selecting candidates for phenotyping, for which genotypic information is also available, from a candidate set and inputting them into the estimation data set and then evaluating accuracy of genomic estimated breeding values for each candidate (i.e. genomic prediction accuracy). The optimized estimation data set is then used as a model to determine genomic estimated breeding values of breeding individuals based purely on genotypic information.

8 Claims, No Drawings

MOLECULAR BREEDING METHODS

CROSS REFERENCE TO RELATED APPLICATIONS

This patent application is a 371 National Stage Entry of PCT patent application no. PCT/US2014/071889, filed on Dec. 22, 2014, which claims the benefit of and priority to U.S. Provisional Application No. 61/921,216, filed Dec. 27, 2013, the entire contents of each is herein incorporated by reference in its entirety.

FIELD

The field relates to molecular genetics and breeding, particularly with regards to the use of genome prediction for making selections as part of a plant or animal breeding program.

BACKGROUND

Genomic prediction (GP) (Meuwissen et al. 2001, *Genetics* 157:1819-1829) is used in plant and animal breeding to predict breeding values for selection purposes, and in human genetics to predict disease risk. It consists of two steps. First, individuals that are phenotyped for a quantitative trait and genotyped at genetic markers are used to estimate marker effects. These individuals are called training individuals; the data set of all individuals is known as training or estimation data set; and the step is either called training or estimation. The estimated marker effects are then used in combination with marker genotypes of a (selection) candidate to predict its breeding value or disease risk. This step is called prediction. The accuracy of breeding values depends strongly on the relatedness between training individuals and selection candidates as demonstrated in (Habier et al. 2013. *Genetics* 194:597-607), and using all phenotypes may reduce accuracy for certain families as demonstrated in HABIER et al. (2013), supra. This may be alleviated by improved statistical methods that model both linkage disequilibrium and co-segregation, as suggested by HABIER et al. (2013) supra. However, no statistical model, which utilizes observed data, can make up for higher accuracies that could have resulted from estimation sets that better match the information needed by specific prediction sets.

Genomic prediction greatly facilitates breeding programs, as simulations and empirical studies have shown its advantages over marker-assisted selection and traditional phenotypic selection (Meuwissen et al. 2001. supra; Bernardo and Yu. 2007. *Crop Science* 47:1082-1090; Lorenzana and Bernardo. 2009. *Theor Appl Genet* 120:151-161). In the near future, animal and plant breeding programs will focus even more on genomic prediction, as genotyping of embryos becomes more feasible and cost-effective. Hence, methods to increase the accuracy of genomic prediction are desirable.

SUMMARY

Methods for selecting individuals in a breeding program are provided herein in which said methods involve constructing an optimized estimation data set by (i) selecting a candidate for phenotyping from a candidate set and placing the candidate into the estimation data set, wherein said genotypic information is available for the candidate; (ii) evaluating accuracy of genomic estimated breeding values for the candidate, (iii) moving the candidate into the optimized estimation data set only if accuracy of genomic estimated breeding value for the candidate is higher than that of other candidates in the candidate set; and (iv) continuing steps (i)-(iii) until an optimized estimation data set is generated; phenotyping candidates in the optimized estimation data set; genotyping breeding individuals at a plurality of markers; obtaining genomic estimated breeding values for the breeding individuals utilizing the phenotypes and genotypes of the candidates in the optimized estimation data set; and selecting breeding individuals based on the genomic estimated breeding values.

The method may further comprise crossing selected breeding individuals. Construction of the optimized estimation data set may be performed using a computer.

Genotypic information for each candidate may be obtained via genotyping or using Monte Carlo simulations.

Breeding individuals may be homozygous, partially homozygous, or heterozygous. Breeding individuals may be plants or animals. If plants, the plants may be selected from the group consisting of: maize, soybean, sunflower, sorghum, canola, wheat, alfalfa, cotton, rice, barley, millet, sugar cane and switchgrass.

The accuracy of genomic estimated breeding values may be obtained using a mathematical formula that inputs marker information from candidates in the candidate set and marker information from parents of one or more populations making up a prediction target. The mathematical formula used is dependent on the prediction target. If the prediction target consists of one population, genomic prediction accuracy, or the accuracy of the genomic estimated breeding values, may be determined using the following formula:

$$\rho_{g_{ij}\hat{g}_{ij}} = \sqrt{\frac{4\sigma_\beta^4 \mathrm{tr}\{ZD_i Z' V_{yy}^{-1}\}}{N_i \sigma_\beta^2}}.$$

$$= \sqrt{\frac{4\sigma_\beta^4 \mathrm{tr}\{G_i V_{yy}^{-1}\}}{N_i}}.$$

where $\sigma_\beta^2$ is the variance of SNP effects, $G_i$ is a genomic relationship matrix weighted by the linkage disequilibrium of population (full-sib family) i, $V_{yy}^{-1}$ is the inverse of the variance-covariance matrix of trait phenotypes of individuals in the estimation data set, and $N_i$ is the number of segregating loci in population i.

If the prediction target consists of more than one population, genomic prediction accuracy, or the accuracy of the genomic estimated breeding values, may be determined using the following formula:

$$\bar{\rho}_{g_{ij}\hat{g}_{ij}} = \frac{1}{N_I} \sum_{i=1}^{N_I} \rho_{g_{ij}\hat{g}_{ij}}$$

which is the average of accuracy within an inbred population across all $N_I$ populations of the prediction target.

Or $$\rho_{g_{ij}\hat{g}_{ij}}^{Iso} = \frac{1}{1-\delta} \sum_{i=1}^{N_I} \rho_{g_{ij}\hat{g}_{ij}}^{1-\delta},$$

where $\delta \in [0,1]$ is called the risk aversion parameter in social welfare economics. If $\delta=0$, then $\rho_{g_{ij}\hat{g}_{ij}}^{Iso}$ acts identical to $\bar{\rho}_{\hat{g}_{ij}\hat{g}_{ij}}$, but as δ increases, populations with high accuracy are weighted lower in favor of populations with lower accuracy. The latter formula can be used to prevent the discrepancy between the accuracy of different populations if the prediction target becomes too large.

If the prediction target consists of a large number of populations (families), the genomic prediction accuracy, or the accuracy of the genomic estimated breeding values, can be replaced in the last two equations by the reliability of $\hat{g}_{ij}$ to make computations more feasable. The equation can be defined as:

$$r_{\hat{g}_{ij}\hat{g}_{ij}} = \rho^2_{\hat{g}_{ij}\hat{g}_{ij}}$$

$$= 4\sigma^2_\beta \frac{1}{N_I} \text{tr}\{\overline{G}V^{-1}_{yy}\}.$$

DETAILED DESCRIPTION

The current disclosure provides methods for optimizing genomic prediction through the creation of optimized estimation data sets. The idea is to identify the best hybrids for training using a mathematical formula that captures the training and prediction steps of genomic prediction and returns either the accuracy of genomic estimated breeding values within a breeding population or an average of accuracy within a breeding population across all populations of a prediction target.

The disclosure of each reference set forth herein is hereby incorporated by reference in its entirety.

As used herein and in the appended claims, the singular forms "a", "an", and "the" include plural reference unless the context clearly dictates otherwise. Thus, for example, reference to "a plant" includes a plurality of such plants, reference to "a cell" includes one or more cells and equivalents thereof known to those skilled in the art, and so forth. As Used Herein:

"Accuracy" as it pertains to genomic estimated breeding values can be defined herein as the correlation between true and estimated breeding values within populations.

"Accuracy of genomic prediction" is used interchangeably herein with accuracy of "genomic estimated breeding values".

As used herein, the term "allele" refers to a variant or an alternative sequence form at a genetic locus. In diploids, single alleles are inherited by a progeny individual separately from each parent at each locus. The two alleles of a given locus present in a diploid organism occupy corresponding places on a pair of homologous chromosomes, although one of ordinary skill in the art understands that the alleles in any particular individual do not necessarily represent all of the alleles that are present in the species.

As used herein, the phrase "associated with" refers to a recognizable and/or assayable relationship between two entities. For example, the phrase "associated with a trait" refers to a locus, gene, allele, marker, phenotype, etc., or the expression thereof, the presence or absence of which can influence an extent, degree, and/or rate at which the trait is expressed in an individual or a plurality of individuals.

As used herein, the term "backcross", and grammatical variants thereof, refers to a process in which a breeder crosses a progeny individual back to one of its parents: for example, a first generation $F_1$ with one of the parental genotypes of the $F_1$ individual.

As used herein, the phrase "breeding population" refers to a collection of individuals from which potential breeding individuals and pairs are selected. A breeding population can be a segregating population.

A "candidate set" is a set of individuals that are genotyped at marker loci used for genomic prediction. A "candidate" may be a hybrid.

As used herein, the term "chromosome" is used in its art-recognized meaning as a self-replicating genetic structure containing genomic DNA and bearing in its nucleotide sequence a linear array of genes.

As used herein, the terms "cultivar" and "variety" refer to a group of similar plants that by structural and/or genetic features and/or performance can be distinguished from other members of the same species.

As used herein, the phrase "determining the genotype" of an individual refers to determining at least a portion of the genetic makeup of an individual and particularly can refer to determining genetic variability in an individual that can be used as an indicator or predictor of a corresponding phenotype. Determining a genotype can comprise determining one or more haplotypes or determining one or more polymorphisms exhibiting linkage disequilibrium to at least one polymorphism or haplotype having genotypic value. Determining the genotype of an individual can also comprise identifying at least one polymorphism of at least one gene and/or at one locus; identifying at least one haplotype of at least one gene and/or at least one locus; or identifying at least one polymorphism unique to at least one haplotype of at least one gene and/or at least one locus.

A "doubled haploid plant" is a plant that is developed by the doubling of a haploid set of chromosomes. A doubled haploid plant is homozygous.

As used herein, the phrase "elite line" refers to any line that is substantially homozygous and has resulted from breeding and selection for superior agronomic performance.

An "estimation data set" or "training data set" is, generally, a set of individuals that are both genotyped for genetic markers and phenotyped for a quantitative or qualitative trait. These individuals are used to estimate the effects of those markers. For our optimization, however, these individuals do not need to be phenotyped yet, because it is the very purpose of this approach to find out what individuals should be phenotyped.

As used herein, the term "gene" refers to a hereditary unit including a sequence of DNA that occupies a specific location on a chromosome and that contains genetic instructions for a particular characteristic or trait in an organism.

As used herein, the phrase "genetic gain" refers to an amount of an increase in performance that is achieved through artificial genetic improvement programs. The term "genetic gain" can refer to an increase in performance that is achieved after one generation has passed (see Allard, 1960).

As used herein, the phrase "genetic map" refers to an ordered listing of loci usually related to the relative positions of the loci on a particular chromosome.

As used herein, the phrase "genetic marker" refers to a nucleic acid sequence (e.g., a polymorphic nucleic acid sequence) that has been identified as being associated with a trait, locus, and/or allele of interest and that is indicative of and/or that can be employed to ascertain the presence or absence of the trait, locus, and/or allele of interest in a cell or organism. Examples of genetic markers include, but are not limited to, genes, DNA or RNA-derived sequences (e.g., chromosomal subsequences that are specific for particular sites on a given chromosome), promoters, any untranslated regions of a gene, microRNAs, short inhibitory RNAs (siRNAs; also called small inhibitory RNAs), quantitative trait loci (QTLs), transgenes, mRNAs, double-stranded RNAs, transcriptional profiles, and methylation patterns.

As used herein, "genomic estimated breeding values" (GEBVs) can refer to a measurable degree to which one or more haplotypes and/or genotypes affect the expression of a phenotype associated with a trait, and it can be considered as a contribution of the haplotype(s) and or genotype(s) to a trait.

The phrase "genomic prediction" refers to methods for increasing genetic gain in a species that employ markers located throughout the genome of the species to predict genomic estimated breeding values (GEBVs) of individuals. Genomic prediction is not based on the use of markers that have previously been identified as being linked to loci (e.g., QTLs) associated with any given trait of interest. Rather, each marker is generally considered as a putative QTL and all the markers are combined to predicting genomic estimated breeding values (GEBVs) of progeny.

As used herein, the term "genotype" refers to the genetic makeup of an organism. Expression of a genotype can give rise to an organism's phenotype (i.e., an organism's observable traits). A subject's genotype, when compared to a reference genotype or the genotype of one or more other subjects, can provide valuable information related to current or predictive phenotypes. The term "genotype" thus refers to the genetic component of a phenotype of interest, a plurality of phenotypes of interest, and/or an entire cell or organism.

As used herein, "haplotype" refers to the collective characteristic or characteristics of a number of closely linked loci within a particular gene or group of genes, which can be inherited as a unit. For example, in some embodiments, a haplotype can comprise a group of closely related polymorphisms (e.g., single nucleotide polymorphisms; SNPs). A haplotype can also be a characterization of a plurality of loci on a single chromosome (or a region thereof) of a pair of homologous chromosomes, wherein the characterization is indicative of what loci and/or alleles are present on the single chromosome (or the region thereof).

As used herein, the term "heterozygous" refers to a genetic condition that exists in a cell or an organism when different alleles reside at corresponding loci on homologous chromosomes.

As used herein, the term "homozygous" refers to a genetic condition existing when identical alleles reside at corresponding loci on homologous chromosomes. It is noted that both of these terms can refer to single nucleotide positions, multiple nucleotide positions (whether contiguous or not), and/or entire loci on homologous chromosomes.

As used herein, the term "hybrid", when used in the context of a plant, refers to a seed and the plant the seed develops into that results from crossing at least two genetically different plant parents.

As used herein, the term "inbred" refers to a substantially or completely homozygous individual or line. It is noted that the term can refer to individuals or lines that are substantially or completely homozygous throughout their entire genomes or that are substantially or completely homozygous with respect to subsequences of their genomes that are of particular interest.

As used herein, the term "introgress", and grammatical variants thereof (including, but not limited to "introgression", "introgressed", and "introgressing"), refer to both natural and artificial processes whereby one or more genomic regions of one individual are moved into the genome of another individual to create germplasm that has a new combination of genetic loci, haplotypes, and/or alleles. Methods for introgressing a trait of interest can include, but are not limited to, breeding an individual that has the trait of interest to an individual that does not and backcrossing an individual that has the trait of interest to a recurrent parent.

As used herein, "linkage disequilibrium" (LD) refers to a derived statistical measure of the strength of the association or co-occurrence of two distinct genetic markers. Various statistical methods can be used to summarize LD between two markers but in practice only two, termed D' and $r^2$, are widely used (see e.g., Devlin & Risch 1995; Jorde, 2000). As such, the phrase "linkage disequilibrium" refers to a change from the expected relative frequency of gamete types in a population of many individuals in a single generation such that two or more loci act as genetically linked loci.

As used herein, the phrase "linkage group" refers to all of the genes or genetic traits that are located on the same chromosome. Within a linkage group, those loci that are sufficiently close together physically can exhibit linkage in genetic crosses. Since the probability of a crossover occurring between two loci increases with the physical distance between the two loci on a chromosome, loci for which the locations are far removed from each other within a linkage group might not exhibit any detectable linkage in direct genetic tests. The term "linkage group" is mostly used to refer to genetic loci that exhibit linked behavior in genetic systems where chromosomal assignments have not yet been made. Thus, in the present context, the term "linkage group" is synonymous with the physical entity of a chromosome, although one of ordinary skill in the art will understand that a linkage group can also be defined as corresponding to a region (i.e., less than the entirety) of a given chromosome.

As used herein, the term "locus" refers to a position on a chromosome of a species, and can encompass a single nucleotide, several nucleotides, or more than several nucleotides in a particular genomic region.

As used herein, the terms "marker" and "molecular marker" are used interchangeably to refer to an identifiable position on a chromosome the inheritance of which can be monitored and/or a reagent that is used in methods for visualizing differences in nucleic acid sequences present at such identifiable positions on chromosomes. A marker can comprise a known or detectable nucleic acid sequence. Examples of markers include, but are not limited to genetic markers, protein composition, peptide levels, protein levels, oil composition, oil levels, carbohydrate composition, carbohydrate levels, fatty acid composition, fatty acid levels, amino acid composition, amino acid levels, biopolymers, starch composition, starch levels, fermentable starch, fermentation yield, fermentation efficiency, energy yield, secondary compounds, metabolites, morphological characteristics, and agronomic characteristics. Molecular markers include, but are not limited to restriction fragment length polymorphisms (RFLPs), random amplified polymorphic DNA (RAPD), amplified fragment length polymorphisms (AFLPs), single strand conformation polymorphism (SSCPs), single nucleotide polymorphisms (SNPs), insertion/deletion mutations (indels), simple sequence repeats (SSRs), microsatellite repeats, sequence-characterized amplified regions (SCARs), cleaved amplified polymorphic sequence (CAPS) markers, and isozyme markers, microarray-based technologies, TAQMAN® markers, ILLUMINA® GOLDENGATE® Assay markers, nucleic acid sequences, or combinations of the markers described herein, which can be employed to define a specific genetic and/or chromosomal location.

A marker may correspond to an amplification product generated by amplifying a nucleic acid with one or more oligonucleotides, for example, by the polymerase chain reaction (PCR). As used herein, the phrase "corresponds to an amplification product" in the context of a marker refers to a marker that has a nucleotide sequence that is the same as or the reverse complement of (allowing for mutations introduced by the amplification reaction itself and/or naturally occurring and/or artificial alleleic differences) an amplification product that is generated by amplifying a nucleic acid with a particular set of oligonucleotides. In some embodiments, the amplifying is by PCR, and the oligonucleotides are PCR primers that are designed to hybridize to opposite strands of a genomic DNA molecule in order to amplify a genomic DNA sequence present between the sequences to which the PCR primers hybridize in the genomic DNA. The amplified fragment that results from one or more rounds of amplification using such an arrangement of primers is a double stranded nucleic acid, one strand of which has a nucleotide sequence that comprises, in 5' to 3' order, the sequence of one of the primers, the sequence of the genomic DNA located between the primers, and the reverse-complement of the second primer. Typically, the "forward" primer is assigned to be the primer that has the same sequence as a subsequence of the (arbitrarily assigned) "top" strand of a double-stranded nucleic acid to be amplified, such that the "top" strand of the amplified fragment includes a nucleotide sequence that is, in 5' to 3' direction, equal to the sequence of the forward primer—the sequence located between the forward and reverse primers of the top strand of the genomic fragment—the reverse-complement of the reverse primer. Accordingly, a marker that "corresponds to" an amplified fragment is a marker that has the same sequence of one of the strands of the amplified fragment.

The term "phenotype" refers to any observable property of an organism, produced by the interaction of the genotype of the organism and the environment. A phenotype can encompass variable expressivity and penetrance of the phenotype. Exemplary phenotypes include but are not limited to a visible phenotype, a physiological phenotype, a susceptibility phenotype, a cellular phenotype, a molecular phenotype, and combinations thereof.

As used herein, the term "plant" refers to an entire plant, its organs (i.e., leaves, stems, roots, flowers etc.), seeds, plant cells, and progeny of the same. The term "plant cell" includes without limitation cells within seeds, suspension cultures, embryos, meristematic regions, callus tissue, leaves, shoots, gametophytes, sporophytes, pollen, and microspores. The phrase "plant part" refers to a part of a plant, including single cells and cell tissues such as plant cells that are intact in plants, cell clumps, and tissue cultures from which plants can be regenerated. Examples of plant parts include, but are not limited to, single cells and tissues from pollen, ovules, leaves, embryos, roots, root tips, anthers, flowers, fruits, stems, shoots, and seeds; as well as scions, rootstocks, protoplasts, calli, and the like.

As used herein, the term "polymorphism" refers to the presence of one or more variations of a nucleic acid sequence at a locus in a population of one or more individuals. The sequence variation can be a base or bases that are different, inserted, or deleted. Polymorphisms can be, for example, single nucleotide polymorphisms (SNPs), simple sequence repeats (SSRs), and Indels, which are insertions and deletions. Additionally, the variation can be in a transcriptional profile or a methylation pattern. The polymorphic sites of a nucleic acid sequence can be determined by comparing the nucleic acid sequences at one or more loci in two or more germplasm entries. As such, in some embodiments the term "polymorphism" refers to the occurrence of two or more genetically determined alternative variant sequences (i.e., alleles) in a population. A polymorphic marker is the locus at which divergence occurs. Exemplary markers have at least two (or in some embodiments more) alleles, each occurring at a frequency of greater than 1%. A polymorphic locus can be as small as one base pair (e.g., a single nucleotide polymorphism; SNP).

As used herein, the term "population" refers to a genetically heterogeneous collection of plants that in some embodiments share a common genetic derivation.

A "prediction target" is a set of selection candidates that come from full-sib inbred populations, where their parents are genotyped at genetic markers.

The term "pre-TC1" refers to the time right after the creation of an inbred, such as for example, a doubled haploid, and before topcross data, i.e. when data from their full-sibs and half-sibs may not be available.

As used herein, the term "progeny" refers to any plant that results from a natural or assisted breeding of one or more plants. For example, progeny plants can be generated by crossing two plants (including, but not limited to crossing two unrelated plants, backcrossing a plant to a parental plant, intercrossing two plants, etc.), but can also be generated by selfing a plant, creating an inbred (e.g. a double haploid), or other techniques that would be known to one of ordinary skill in the art. As such, a "progeny plant" can be any plant resulting as progeny from a vegetative or sexual reproduction from one or more parent plants or descendants thereof. For instance, a progeny plant can be obtained by cloning or selfing of a parent plant or by crossing two parental plants and include selfings as well as the $F_1$ or $F_2$ or still further generations. An $F_1$ is a first-generation progeny produced from parents at least one of which is used for the first time as donor of a trait, while progeny of second generation ($F_2$) or subsequent generations ($F_3$, $F_4$, and the like) are in some embodiments specimens produced from selfings (including, but not limited to double haploidization), intercrosses, backcrosses, or other crosses of $F_1$ individuals, $F_2$ individuals, and the like. An $F_1$ can thus be (and in some embodiments, is) a hybrid resulting from a cross between two true breeding parents (i.e., parents that are true-breeding are each homozygous for a trait of interest or an allele thereof, and in some embodiments, are inbred), while an $F_2$ can be (and in some embodiments, is) a progeny resulting from self-pollination of the $F_1$ hybrids.

As used herein, the phrase "single nucleotide polymorphism", or "SNP", refers to a polymorphism that constitutes a single base pair difference between two nucleotide sequences. As used herein, the term "SNP" also refers to differences between two nucleotide sequences that result from simple alterations of one sequence in view of the other that occurs at a single site in the sequence. For example, the term "SNP" is intended to refer not just to sequences that differ in a single nucleotide as a result of a nucleic acid substitution in one as compared to the other, but is also intended to refer to sequences that differ in 1, 2, 3, or more nucleotides as a result of a deletion of 1, 2, 3, or more nucleotides at a single site in one of the sequences as compared to the other. It would be understood that in the case of two sequences that differ from each other only by virtue of a deletion of 1, 2, 3, or more nucleotides at a single site in one of the sequences as compared to the other, this same scenario can be considered an addition of 1, 2, 3, or more nucleotides at a single site in one of the sequences as compared to the other, depending on which of the two sequences is considered the reference sequence. Single site insertions and/or deletions are thus also considered to be encompassed by the term "SNP".

The term "test-and-shelf" refers to the state in which inbreds are not selected/chosen for field testing but are kept until data from their full- and/or half-sibs are available.

As used herein, the term "tester" refers to a line used in a testcross with one or more other lines wherein the tester and the line(s) tested are genetically dissimilar. A tester can be an isogenic line to the crossed line.

The term "topcross" refers to a cross between a parent being tested and a tester, usually a homozygous line. A "topcross test" is a progeny test derived by crossing each parent with the same tester, usually a homozygous line. The parent being tested can be an open-pollinated variety, a cross, or an inbred line.

As used herein, the terms "trait" and "trait of interest" refer to a phenotype of interest, a gene that contributes to a phenotype of interest, as well as a nucleic acid sequence associated with a gene that contributes to a phenotype of interest. Any trait that would be desirable to screen for or against in subsequent generations can be a trait of interest.

A "trait" may refer to a physiological, morphological, biochemical, or physical characteristic of a plant or a particular plant material or cell. In some instances, this characteristic is visible to the human eye, or can be measured by biochemical techniques.

Exemplary, non-limiting traits of interest in corn include yield, disease resistance, agronomic traits, abiotic traits, kernal composition (including, but not limited to protein, oil, and/or starch composition), insect resistance, fertility, silage, and morphological traits. In some embodiments, two or more traits of interest are screened for and/or against (either individually or collectively) in progeny individuals.

Turning to the Embodiments:

Methods to select individuals as part of a breeding program by optimizing genomic prediction are provided herein in which said methods comprise constructing an optimized estimation data set by selecting candidates for phenotyping from a candidate set; placing the candidate into the estimation data set; and evaluating accuracy of genomic estimated breeding values for each candidate (i.e. genomic prediction accuracy). The optimization approach relies on the principle that the accuracy of breeding values depends strongly on the relatedness between training individuals and selection candidates (Habier et al. 2013. supra). The optimized estimation data set may be constructed using a computer.

Candidates can be genotyped using markers but if not genotyped, Monte Carlo simulations can be used to evaluate the potential of a specific type or group of individuals as to the genomic prediction accuracy. The candidates may or may not be related to populations in the prediction target.

A candidate is only moved into the optimized estimation data set permanently if the accuracy of genomic estimated breeding values for the candidate is higher than that of other candidates in the candidate set. The accuracy of genomic estimated breeding values is obtained using a mathematical formula that incorporates estimation and prediction steps of genomic prediction and returns the accuracy of genomic estimated breeding values, measured for individuals within a population, for all populations in the prediction target. That accuracy is connected to or pertains to an estimation data set containing individuals from the candidate set. Thus, the mathematical formula can be regarded as taking a set of individuals from the candidate set and the populations of the prediction target as input and returning the genomic prediction accuracy, or accuracy of the genomic estimated breeding values, for individuals of the prediction target.

Breeding populations of the prediction target are described in mathematical-genetical terms, i.e. marker genotypes of inbred parents, and genetic map distances of markers are used to derive a pattern of linkage disequilibrium (LD) between marker loci for each population in the prediction target. Because each cross has different parents and each parent has different marker genotypes, each breeding population has a unique LD pattern. The use of LD in the formula follows naturally from derivation of the mathematical formula and definitions of both LD and co-segregation of allele states from parents to inbred offspring as shown in the EXAMPLES below. The advantage of using only marker genotypes of parents is that the optimization approach can be used to identify optimal training data sets for future breeding cross populations, be they $F_1$ or $F_2$ derived. In addition, using those LD patterns avoids the problem that is encountered in other optimization approaches (Maenhout et al. 2010 Theor Appl Genet. 120:415-427; Rincent et al. 2012. *Genetics* 192:715-728), this is deciding which of the genotyped inbreds are declared either selection candidates or candidates for training. Using linkage disequilibrium means that the future selection candidates coming from populations in the prediction target do not need to be genotyped for this optimization approach. Thus, it allows optimizing training data sets years before those populations are (actually created) available for selection; and it does not require nor is limited by the arbitrary partition of genotyped individuals in candidates and selection candidates, as with other approaches.

The core of the optimization approach is a mathematical formula for the accuracy of genomic estimated breeding values within populations of the prediction target, which captures the process of genomic prediction consisting of assembling an estimation data set, running the estimation data set through genomic prediction software, and using estimated single nucleotide polymorphism effects together with the markers of the prediction target to estimate genomic estimated breeding values. Determination of the mathematical formula to use is dependent on the prediction target.

If the prediction target consists of one population (e.g. one full-sib family), genomic prediction accuracy, or the accuracy of the genomic estimated breeding values, is determined using the following formula:

$$\rho_{g_{ij}\hat{g}_{ij}} = \sqrt{\frac{4\sigma_\beta^2 tr\{G_i V_{yy}^{-1}\}}{N_i}}$$

where $\sigma_\beta^2$ is the variance of SNP effects, $G_i$ is a genomic relationship matrix weighted by the linkage disequilibrium of population (full-sib family) i, $V_{yy}^{-1}$ is the inverse of the variance-covariance matrix of trait phenotypes of individuals in the estimation data set, and $N_i$ is the number of segregating loci in population i.

If the prediction target consists of more than one population (i.e. more than one full sib family), genomic prediction accuracy, or the accuracy of the genomic estimated breeding values, is determined using the following formula:

$$\bar{\rho}_{g_{ij}\hat{g}_{ij}} = \frac{1}{N_I}\sum_{i=1}^{N_I}\rho_{g_{ij}\hat{g}_{ij}} \tag{1}$$

which is the average of accuracy within an inbred population across all $N_I$ populations of the prediction target.

or $$\rho^{Iso}_{g_{ij}\hat{g}_{ij}} = \frac{1}{1-\delta}\sum_{i=1}^{N_I}\rho^{1-\delta}_{g_{ij}\hat{g}_{ij}},$$

where $\delta\in[0,1]$ is called the risk aversion parameter in social welfare economics. If $\delta=0$, then $\rho^{Iso}_{g_{ij}\hat{g}_{ij}}$ acts identical to $\rho_{g_{ij}\hat{g}_{ij}}$, but as $\delta$ increases, populations with high accuracy are weighted lower in favor of populations with lower accuracy. The latter formula can be used to prevent that the discrepancy between the accuracy of different populations in the prediction target becomes too large.

If the prediction target consists of a large number of populations (families) the genomic prediction accuracy, or the accuracy of the genomic estimated breeding values, can be replaced in the last two equations by the reliability of $\hat{g}_{ij}$ to make computations more feasable. The equation can be defined as $$r_{g_{ij}\hat{g}_{ij}} = \rho^2_{g_{ij}\hat{g}_{ij}}$$
$$= 4\sigma^2_\beta \frac{1}{N_I} tr\{\overline{G}V_{yy}^{-1}\}.$$

Phenotypes of the candidates in the optimized estimation data set, at one or more traits, are obtained, and the phenotypes and genotypes of the candidates in the optimized estimation data set can be used to obtain genomic estimated breeding values for breeding individuals. Essentially, the phenotypes and genotypes of the candidates in the optimized estimation data set are used to parameterize a statistical model such that genomic estimated breeding values can be determined by the genotype of a breeding individual using information contained within the optimized estimation data set.

Breeding individuals are the individuals in a breeding program upon which selection is being imposed. (It is important to note that the breeding individuals and the candidates in the optimized estimation data set are of the same species.) Breeding individuals can be homozygous, partially homozygous, or heterozygous. If homozygous, the breeding individuals may be inbreds or doubled haploids.

The breeding individuals are genotyped at a plurality of markers, and using the optimized genomic prediction program, are given genomic estimated breeding values, which can serve as a means for comparison between the breeding individuals (and allows ranking of the breeding individuals). Breeding individuals with desirable genomic estimated breeding values can be selected for further plant improvement, whether that be selecting individuals as parents of a cross or selecting one or more individuals to grow for further evaluation. Selected breeding individuals may be in the top 25%, 24%, 23%, 22%, 21%, 20%, 19%, 18%, 17%, 16%, 15%, 14%, 13%, 12%, 11%, 10%, 9%, 8%, 7%, 6%, 5%, 4%, 3%, 2%, or 1% with respect to the entire pool of breeding individuals and their respective genomic estimated breeding values. If the breeding individuals are selected for crossing, the crossing may be performed to produce a hybrid (such as, for example, in maize).

Applications

The approach is not only applicable to plant breeding, but also animal breeding. It is an improved method of making selections of breeding individuals using an optimized planning tool which allows breeding individuals to be selected based solely on the use of markers, enabling the more efficient use of field resources (i.e. higher accuracy for the same amount of resources used or similar accuracy for a decreased amount of resources used).

For example, in corn, it can be used at all selection stages of product development, the greatest utility of which is within-family ranking of doubled haploids in the early stages of inbred development because pedigree information cannot discriminate full-sibs and phenotypic information is limited or not yet available. In the first stage of selection (Pre-TC1), breeders select TC1 entries from a large number of doubled haploid populations, with each family containing tens or even hundreds of doubled haploids. Per se data are used initially, but then breeders have the option to either choose TC1 entries randomly, by maximum diversity, or by genomic prediction using data from TC1 or marker enhanced pedigree selection (MEPS) experiments of previous years. Genomic prediction in Pre-TC1 can also be used to directly select TC2 entries and 'jump' over TC1.

Any of the methods disclosed herein may be used in combination with any of the methods disclosed in U.S. application Ser. Nos. 14/473,183, 14/473,074, and 14/473,183.

Further embodiments include methods for enhanced genome wide prediction to select inbreds and hybrids with drought tolerance to improve crop yield under drought conditions and parity yield performance under more favorable environmental conditions; enhanced multi-trait genome wide prediction for selecting inbreds and hybrids with improved yield and agronomic performance for specific target environments; enhanced genome wide prediction for selection of inbreds and hybrids with improved yield and agronomic performance for target geographies where genotype-by-environment interactions are important; and enhanced genome wide prediction of the combined effects of transgenic and native genetic variation on inbred and hybrid yield and agronomic performance for each of the methods described above.

EXAMPLES

The present invention is further illustrated in the following Examples, in which parts and percentages are by weight and degrees are Celsius, unless otherwise stated. It should be understood that these Examples, while indicating embodiments of the invention, are given by way of illustration only. From the above discussion and these Examples, one skilled in the art can ascertain the essential characteristics of this invention, and without departing from the spirit and scope thereof, can make various changes and modifications of the invention to adapt it to various usages and conditions. Thus, various modifications of the invention in addition to those shown and described herein will be apparent to those skilled in the art from the foregoing description. Such modifications are also intended to fall within the scope of the appended claims.

Example 1

Derivation of the Optimization Criterion
Accuracy within Inbred Populations

The accuracy within a population is defined herein as the correlation between true and estimated breeding values, $g_{ij}$ and $\hat{g}_{ij}$, respectively, of an individual j that is randomly drawn from inbred population i, and can be written as $$\rho_{g_{ij}\hat{g}_{ij}} = \frac{\text{Cov}(g_{ij}, \hat{g}_{ij})}{\sqrt{\text{Var}(g_{ij})\text{Var}(\hat{g}_{ij})}}.$$

Under the assumption that the statistical model is identical to the true genetic model, which will be detailed below, $\text{Cov}(g_{ij}, \hat{g}_{ij}) = \text{Var}(\hat{g}_{ij})$, so that the above formula reduces to $$\rho_{g_{ij}\hat{g}_{ij}} = \sqrt{\frac{\text{Var}(\hat{g}_{ij})}{\text{Var}(g_{ij})}}.$$

In the following, the variances of $g_{ij}$ and $\hat{g}_{ij}$ are derived.

Genetic and Statistical Models

It is good practice in quantitative genetics to distinguish the statistical model used for the statistical analyses of training data from the true genetic model. While the statistical model can be clearly specified by the researcher, the true genetic model represents assumptions about the true, but unknown nature of the data such as number of quantitative trait loci, mode of inheritance, gene actions, and gene interactions. In most genetic studies both types of models are assumed to be identical. For the optimization approach described herein, genetic and statistical models are assumed identical. For simplicity purposes, derivations presented herein are for $F_1$-derived inbreds, but one of ordinary skill in the art will understand that the derivations can be applied to other populations in the prediction target as well.

Genetic Model and Variance of a True Breeding Value

The true breeding value, $g_{ij}$, of selection candidate j from inbred population, i, that is in the prediction target can be written as $$g_{ij} = 2z'_{ij}\beta,$$

where $z'_{ij}$ denotes a vector of allele states at K SNPs. Allele states can take the values 0 or 1 and are adjusted by the expected allele frequency within a bi-parental $F_1$-derived inbred population so that the expected value of $z'_{ij}$ is zero. At loci where the two parents are polymorph (i.e., one parent has allele state 0 and the other parent has allele state 1), the expected allele frequency is 0.5, while it is 0 or 1 where parents are monomorph (i.e., both parents have identical allele states). The variance of adjusted allele states is 0.25 at polymorphic loci and 0 elsewhere. The vector $\beta$ contains random SNP effects with mean zero and variance $I\sigma_\beta^2$. The variance $\sigma_\beta^2$ will be detailed later, after the statistical model is presented. It is also good practice in statistics to specify the expected value and variance of a random variable or model; hence, the expected value of $g_{ij}$ is $$E(g_{ij}) = E(2z'_{ij}\beta)$$
$$= E_{z_{ij}}\left[E_{\beta|z_{ij}}(2z'_{ij}\beta|z_{ij})\right]$$
$$= 0,$$

because $E(z_{ij}) = 0$ and $E(\beta) = 0$. The variance of $g_{ij}$ is $$\text{Var}(g_{ij}) = \text{Var}(2z'_{ij}\beta)$$
$$= E_{z_{ij}}\left[\text{Var}_{\beta|z_{ij}}(2z'_{ij}\beta|z_{ij})\right] + \text{Var}_{z_{ij}}\left[E_{\beta|z_{ij}}(2z'_{ij}\beta|z_{ij})\right]$$
$$= E_{z_{ij}}[4z'_{ij}z_{ij}\sigma_\beta^2] + \text{Var}_{z_{ij}}[0]$$
$$= 4\sigma_\beta^2 E_{z_{ij}}\left[\sum_{k=1}^{K} z_{ijk}^2\right]$$
$$= 4\sigma_\beta^2 \sum_{k=1}^{K} E(z_{ijk}^2)$$
$$= 4\sigma_\beta^2 N_i \cdot 0.25$$
$$= N_i \sigma_\beta^2,$$

where $N_i$ is the number of polymorphic SNPs of inbred population i.

Generalization

If SNP effects have mean $\mu_\beta$ and variance-covariance matrix $V_\beta$, then $$\text{Var}(g_{ij}) = \text{Var}(2z'_{ij}\beta)$$
$$= E_{z_{ij}}\left[\text{Var}_{\beta|z_{ij}}(2z'_{ij}\beta|z_{ij})\right] + \text{Var}_{z_{ij}}\left[E_{\beta|z_{ij}}(2z'_{ij}\beta|z_{ij})\right]$$
$$= E_{z_{ij}}[4z'_{ij}V_\beta z_{ij}] + \text{Var}_{z_{ij}}[2z'_{ij}\mu_\beta]$$
$$= 4tr[V_\beta \text{Var}(z_{ij})] + E(z'_{ij})V_\beta E(z_{ij}) + 4\mu'_\beta \text{Var}(z_{ij})\mu_\beta$$
$$= 4tr[V_\beta \text{Var}(z_{ij})] + 4\mu'_\beta \text{Var}(z_{ij})\mu_\beta,$$

where $$\text{Var}(z_{ij}) = \begin{bmatrix} \text{Var}(z_{ij1}) & \text{Cov}(z_{ij1}, z_{ij1}) & \cdots & \text{Cov}(z_{ij1}, z_{ijK}) \\ \text{Cov}(z_{ij2}, z_{ij1}) & \text{Var}(z_{ij2}) & \cdots & \text{Cov}(z_{ij2}, z_{ijK}) \\ \vdots & \vdots & \ddots & \vdots \\ \text{Cov}(z_{ijK}, z_{ij1}) & \text{Cov}(z_{ijK}, z_{ij2}) & \cdots & \text{Var}(z_{ijK}) \end{bmatrix},$$

$\text{Var}(z_{ijk})$ equals 0.25 or 0, and $\text{Cov}(z_{ijk}, z_{ijk'})$ is derived below. If $\mu_\beta = 0$, and $V_\beta$ is a diagonal matrix $D_\beta = \{\sigma_{\beta_k}^2\}$, then $$\text{Var}(g_{ij}) = \sum_{k=1}^{K} I_{poly}\sigma_{\beta_k}^2,$$

where $I_{poly}$ is an indicator that is 1 if SNP k is polymorph and 0 otherwise.

Statistical Model

The statistical model for N hybrid phenotypes can be written as $$y = Xb + Z\beta + e,$$

where y is the vector of phenotypes, X is a known incidence matrix for fixed environmental effects in vector b, Z is an N×K matrix of observed genotype scores, $\beta$ is a K×1 vector of SNP effects treated as random with mean zero and variance $I\sigma_\beta^2$, and e is a vector containing random residual effects with mean zero and variance $I\sigma_e^2$. Thus, the expected value and variance of y are $E(y) = Xb$ and $\text{Var}(y) = V_{yy} = ZZ'\sigma_\beta^2 + I\sigma_e^2$, respectively. The common variance for all SNP effects $\sigma_\beta^2$ is assumed to be a function of the additive-genetic variance of hybrid performance, $\sigma_a^2$, as $$\sigma_\beta^2 = \frac{\sigma_a^2}{c},$$

where c is a constant that needs to be specified. That constant determines how much each SNP effect is shrinked towards zero in the statistical analysis, and therefore can have a decisive effect on the estimated effects and thereby on the accuracy of selection.

Statistical Method

The genomic estimated breeding value of selection candidate j can be estimated by Best Linear Unbiased Prediction (BLUP) as $$\hat{g}_{ij} = v'_{gy} V_{yy}^{-1}(y - X\hat{b}),$$

where $v'_{gy}$ is a row-vector of genetic relationships between selection candidate j and the training individuals. Assuming that SNP genotypes were observed for both selection candidate and training individuals, $v'_{gy}$ is derived as $$\text{Cov}(g_{ij}, y') = \text{Cov}(2z'_{ij}\beta, \beta'Z')$$
$$= 2z'_{ij} V_\beta Z'.$$

Thus, $$v'_{gy} = \begin{cases} 2z'_{ij} Z' \sigma_\beta^2 & V_\beta = I\sigma_\beta^2 \\ 2z'_{ij} D_\beta Z' & V_\beta = D_\beta \end{cases}.$$

The first case is usually assumed in Genomic BLUP (HABIER et al., 2013 supra), whereas the second one is more similar to BayesA and BayesB (MEUWISSEN et al. 2001. *Genetics* 157:1819-1829). The term $V_{yy}^{-1}(y - X\hat{b})$ can be re-written as $$Py = V_{yy}^{-1}[I - X(X'V_{yy}^{-1}X)^{-1}X'V_{yy}^{-1}]y,$$

hence, $$\hat{g}_{ij} = v'_{gy} Py.$$

Variance of Estimated Breeding Values

First, the variance of $\hat{g}_{ij}$ given $z'_{ij}$ can be written as $$\text{Var}(\hat{g}_{ij} \mid z_{ij}) = v'_{gy} P V_{yy} P' v_{gy}$$
$$= 4z'_{ij} V_\beta Z' P V_{yy} P' Z V_\beta z_{ij},$$

and the expected value of $\hat{g}_{ij}$ given $z'_{ij}$, $$E(\hat{g}_{ij} \mid z_{ij}),$$

is zero, because PXb=0. Consequently, $$\text{Var}(\hat{g}_{ij}) = E_{z_{ij}}[\text{Var}(\hat{g}_{ij} \mid z_{ij})] + \text{Var}_{z_{ij}}[E(\hat{g}_{ij} \mid z_{ij})]$$
$$= E_{z_{ij}}[4z'_{ij} V_\beta Z' P V_{yy} P' Z V_\beta z_{ij}] + \text{Var}_{z_{ij}}[0]$$
$$= 4\text{tr}\left\{E_{z_{ij}}(z_{ij} z'_{ij}) V_\beta Z' P V_{yy} P' Z V_\beta\right\}.$$

Further, $$E(z_{ij}, z'_{ij}) = E(\{z_{ijk} z'_{ijk'}\}) = E\left(\begin{bmatrix} z_{ij1}^2 & z_{ij1} z_{ij2} & \cdots & z_{ij1} z_{ijK} \\ z_{ij2} z_{ij1} & z_{ij2}^2 & \cdots & z_{ij2} z_{ijK} \\ \vdots & \vdots & \ddots & \vdots \\ z_{ijK} z_{ij1} & z_{ijK} z_{ij2} & \cdots & z_{ijK}^2 \end{bmatrix}\right),$$

where $z_{ijk}$ and $z_{ijk'}$ denote allele states of individual j of population i at SNPs k and k', respectively. The expected value of $z_{ijk}^2$ is zero for monomorphic loci, and is $\text{Var}(z_{ijk}) = 0.25$ for polymorphic loci. The cross-product between allele states at two monomorphic loci is zero and at two polymorphic SNPs k and k' it can be expressed as linkage disequilibrium (LD) within population, which can be evaluated here as $$D_{ikk'} = \text{Cov}(z_{ijk}, z_{ijk'})$$
$$= E(z_{ijk}, z_{ijk'}),$$

because allele states were adjusted by their expected values, the allele frequencies. The LD results entirely from co-segregation of allele states at different loci from parents to inbred offspring. Hence, this within-family LD can be derived by allele origin states of inbreds as follows. As the non-adjusted allele states $z^*_{ijk}$ and $z^*_{ijk'}$ are Bernoulli random variables, the derivation of $E(z_{ijk} z_{ijk'})$ needs to focus only on cases where $z^*_{ijk} = z^*_{ijk'} = 1$. Depending on the non-adjusted allele states of the inbred parents, four different cases exist, which are summarized in Table 1.

TABLE 1

Expected cross-product of non-adjusted allele states at SNPs k and k' of inbreds from a bi-parental $F_1$-derived population conditional on the non-adjusted allele states of the two parents. $O_{ijk}$ and $O_{ijk'}$ denote parental allele origins of the allele states of inbred j of population i, and $c_{kk'}$ denotes the recombination frequency between SNPs k and k'.

| | Allele states of | | | | |
|---|---|---|---|---|---|
| | Parent A | | Parent B | | |
| Case | $z^*_{Ak}$ | $z^*_{Ak'}$ | $z^*_{Bk}$ | $z^*_{Bk'}$ | $E(z^*_{ijk} z^*_{ijk'} \mid z^*_{Ak}, z^*_{Ak'}, z^*_{Bk}, z^*_{Bk'})$ |
| 1 | 0 | 0 | 1 | 1 | $0.5 \cdot \Pr(O_{ijk} = B, O_{ijk'} = B) = 0.5(1 - c_{kk'})$ |
| 2 | 0 | 1 | 1 | 0 | $0.5 \cdot \Pr(O_{ijk} = B, O_{ijk'} = A) = 0.5 c_{kk'}$ |
| 3 | 1 | 0 | 0 | 1 | $0.5 \cdot \Pr(O_{ijk} = A, O_{ijk'} = B) = 0.5 c_{kk'}$ |
| 4 | 1 | 1 | 0 | 0 | $0.5 \cdot \Pr(O_{ijk} = A, O_{ijk'} = A) = 0.5(1 - c_{kk'})$ |

LD within a bi-parental population with known SNP genotypes of the parents can then be calculated between segregating loci as $$D_{ikk'} = E(z^*_{ijk} z^*_{ijk'} \mid z^*_{Ak}, z^*_{Ak'}, z^*_{Bk}, z^*_{Bk'}) - E(z^*_{ijk}) E(z^*_{ijk'})$$
$$= E(z^*_{ijk} z^*_{ijk'} \mid z^*_{Ak}, z^*_{Ak'}, z^*_{Bk}, z^*_{Bk'}) - 0.5 \cdot 0.5$$
$$= \begin{cases} 0.5(1 - c_{kk'}) - 0.25 & \text{Cases 1 and 4} \\ 0.5 c_{kk'} - 0.25 & \text{Cases 2 and 3} \end{cases}.$$

-continued $$= \begin{cases} 0.25(1-2c_{kk'}) & Cases 1 and 4 \\ -0.25(1-2c_{kk'}) & Cases 2 and 3 \end{cases}.$$

If SNPs k and k' are unlinked, i.e., $c_{kk'}=0.5$, then $D_{ikk'}=0$; but if they are tightly linked, i.e., $c_{kk'} \rightarrow 0$, then $$D_{ikk'} = \begin{cases} 0.25 & Cases 1 and 4 \\ -0.25 & Cases 2 and 3 \end{cases},$$

and LD measured as $r_{kk'}^2$ equals 1, because $\text{Var}(z_{ijk})=\text{Var}(z_{ijk'})=0.25$. In general, using Haldane's mapping function to replace recombination frequency $c_{kk'}$ by $0.5(1-e^{-2 \cdot d})$ gives $$D_{ikk'} = \begin{cases} 0.25e^{-2d} & Cases 1 and 4 \\ -0.25e^{-2d} & Cases 2 and 3 \end{cases},$$

where d denotes the map distance between SNPs k and k' in Morgan. As a side, it follows that $r_{kk'}^2=e^{-4 \cdot d}$. As a result, $$D_i E(z_{ij} z'_{ij}) = \text{Var}(z_{ij}) = \begin{bmatrix} \text{Var}(z_{ijk}) & a_{i12} D_{i12} & \cdots & a_{i1K} D_{i1K} \\ a_{i21} D_{i21} & \text{Var}(z_{ijk}) & \cdots & a_{i2K} D_{i2K} \\ \vdots & \vdots & \ddots & \vdots \\ a_{iK1} D_{iK1} & a_{iK2} D_{iK2} & \cdots & \text{Var}(z_{ijk}) \end{bmatrix},$$

where $$a_{ikk'} = \begin{cases} 1 & Cases 1 and 4 \\ -1 & Cases 2 and 3 \end{cases}.$$

In conclusion, $$\text{Var}(\hat{g}_{ij})=4tr\{D_i V_\beta Z'PV_{yy}P'ZV_\beta\}.$$

If selection index methodology is used instead of BLUP and $V_\beta = I\sigma_\beta^2$, the formula reduces to $$\text{Var}(\hat{g}_{ij}) = 4\sigma_\beta^4 tr\{D_i Z' V_{yy}^{-1} Z\}$$
$$= 4\sigma_\beta^4 tr\{ZD_i Z' V_{yy}^{-1}\},$$

which reduces the number of calculations and thereby run-time, while the accuracy is only marginally affected. Note that for each inbred population in the prediction target a different $D_i$ needs to be calculated. The matrix product $ZD_i Z'$ can be regarded as a genomic relationship matrix $G_i$ that results from weighing marker scores by $D_i$ and that is thereby specific to each population i. $G_i$ is calculated for each population i before the iterative optimization algorithm starts (described below).

Optimization Criteria

The accuracy of $\hat{g}_{ij}$ can now be written as $$\rho_{g_{ij}\hat{g}_{ij}} = \sqrt{\frac{4\sigma_\beta^2 tr\{ZD_i Z' V_{yy}^{-1}\}}{N_i \sigma_\beta^2}}$$
$$= \sqrt{\frac{4\sigma_\beta^2 tr\{G_i V_{yy}^{-1}\}}{N_i}}.$$

If there is more than one population in the prediction target, the optimization criterion becomes $$\bar{\rho}_{g_{ij}\hat{g}_{ij}} = \frac{1}{N_I} \sum_{i=1}^{N_I} \rho_{g_{ij}\hat{g}_{ij}} \quad (1)$$

which is the average of accuracy within an inbred population across all $N_I$ populations of the prediction target. A problem that may arise from using this average is that some populations may have a large accuracy, while others may have a low accuracy, a problem found in social welfare economics. Therefore, equation (1) may be replaced by an iso-elastic function as $$\rho_{g_{ij}\hat{g}_{ij}}^{Iso} = \frac{1}{1-\delta} \sum_{i=1}^{N_I} \rho_{g_{ij}\hat{g}_{ij}}^{1-\delta},$$

where $\delta \in [0,1]$ is called the risk aversion parameter in social welfare economics. If $\delta=0$, then $\rho_{g_{ij}\hat{g}_{ij}}^{Iso}$ acts identical to $\rho_{g_{ij}\hat{g}_{ij}}$, but as $\delta$ increases, populations with high accuracy are weighted lower in favor of populations with lower accuracy.

Another problem of using $\rho_{g_{ij}\hat{g}_{ij}}$ is that $G_i$ has to be stored for each population and the trace function has to be evaluated for each population in every iteration of the optimization algorithm, which are both huge computational burdens as the number of populations increases. To solve this problem analytically, the accuracy of $\hat{g}_{ij}$ can be replaced by the reliability of $\hat{g}_{ij}$ defined as $$r_{g_{ij}\hat{g}_{ij}} = \rho_{g_{ij}\hat{g}_{ij}}^2$$
$$= \frac{4\sigma_\beta^2 tr\{G_i V_{yy}^{-1}\}}{N_i}.$$

Then the average of $r_{g_{ij}\hat{g}_{ij}}$ can be written as $$\bar{r}_{g_{ij}\hat{g}_{ij}} = 4\sigma_\beta^2 \frac{1}{N_I} \sum_{i=1}^{N_I} tr\left\{\frac{1}{N_i} ZD_i Z' V_{yy}^{-1}\right\}$$
$$= 4\sigma_\beta^2 \frac{1}{N_I} tr\left\{\sum_{i=1}^{N_I} \frac{1}{N_i} ZD_i Z' V_{yy}^{-1}\right\}$$
$$= 4\sigma_\beta^2 \frac{1}{N_I} tr\left\{Z\left(\sum_{i=1}^{N_I} \frac{1}{N_i} D_i\right) Z' V_{yy}^{-1}\right\}$$
$$= 4\sigma_\beta^2 \frac{1}{N_I} tr\{Z\bar{D}_i Z' V_{yy}^{-1}\}$$
$$= 4\sigma_\beta^2 \frac{1}{N_I} tr\{\bar{G} V_{yy}^{-1}\}.$$

Now only $\bar{G}$ has to be stored and the trace function needs to be evaluated only once per iteration irrespective of the number of populations in the prediction target. Although the reliability is widely accepted and commonly used in breeding applications instead of the accuracy, because it describes the amount of genetic variance explained by the estimated breeding values, it is not exactly the desired optimization criterion anymore. Nevertheless, analyses using both criterions have shown that the optimization performance is not affected much.

Example 2

Optimization Approach

To identify optimal hybrids, an iterative forward selection algorithm is implemented that starts with an empty estimation data set. In each iteration, hybrids of the candidate set are put into the estimation data set one by one and the increase in accuracy of genomic estimated breeding values for the prediction target is recorded for each hybrid. The hybrid that results in the largest increase in accuracy is moved permanently into the estimation data set, while all other hybrids remain in the candidate set. This is repeated until the desired estimation data set size is reached.

The data required to describe the prediction target are the marker genotypes of the parents of breeding crosses. This has the advantage that optimizations for future crosses can be conducted. The data required to describe the hybrid candidates are the genotypes of their inbred parents. However, even if these genotypes are not available, a priori studies can be conducted by simulations using real marker data. The advantage is that any type of cross can be evaluated regarding its potential to increase accuracy of genomic estimated breeding values.

Example 3

Real Data Results

A Meta-data set comprising approximately 1,000 hybrids from 16 bi-parental Non-Stiff Stalk populations was used to study optimized estimation data sets versus randomly assembled estimation data sets. The procedure for obtaining optimized estimation data sets was performed as described in EXAMPLE 2 using the mathematical formulas described in EXAMPLE 1 for determining the accuracy of genomic estimated breeding values within populations of the prediction target.

The populations were split into a candidate set and a validation set, and two separate scenarios were run. In the first scenario, each population was optimized separately, and the candidates were either full- or half-sibs. In the second scenario, all populations were optimized simultaneously, and there were ~800 candidates from all populations. The accuracy of genomic estimated breeding values for yield from Scenarios 1 and 2 are presented in Tables 2 and 3, respectively. Scenario 2 was also performed for the grain moisture trait. Results are shown in Table 4.

TABLE 2

Scenario 1: Correlation between observed and predicted yield within population

| Case | No. of full sibs | No. of half sibs | Estimation data set size | Accuracy of genomic estimated breeding values | |
|---|---|---|---|---|---|
| | | | | Optimized | Random |
| 1 | 5 | 0 | 5 | 0.16 | 0.09 |
| 2 | 0 | 50 | 50 | 0.23 | 0.17 |
| 3 | 5 | 50 | 55 | 0.27 | 0.21 |

TABLE 3

Scenario 2: Correlation between observed and predicted yield within population

| Estimation data set size | Optimized | Random |
|---|---|---|
| 100 | 0.2 | 0.23 |
| 200 | 0.3 | 0.26 |
| 300 | 0.36 | 0.31 |
| 400 | 0.37 | 0.34 |

TABLE 4

Scenario 2: Correlation between observed and predicted grain moisture within population

| Estimation data set size | Optimized | Random |
|---|---|---|
| 100 | 0.42 | 0.36 |
| 200 | 0.5 | 0.42 |
| 300 | 0.53 | 0.49 |
| 400 | 0.54 | 0.53 |

Results showed that optimized estimation data sets give higher accuracies of genomic estimated breeding values (with the exception of scenario 2 in conjunction with a smaller estimation data set size for the yield trait). One reason is that the approach identifies hybrids of the most informative full-sibs of doubled haploids in the prediction target, which are doubled haploids where half of the genome comes from one parent of a bi-parental breeding cross and the other half from the other parent. Another reason is that the optimization approach identifies the best half-sibs for estimation by selecting both maternal and paternal half-sibs if available. Finally, the optimization approach utilizes the family structure within the prediction target by selecting those candidates into the estimation data set that increase accuracy for as many populations of the prediction target as possible.

Example 4

Simulation Results

Simulations were conducted to compare accuracies of genomic prediction for both Pre-TC1 and Test-and-Shelf doubled haploids obtained by the optimization approach as compared to those obtained from maximum diversity selection and random selection for an estimation data set size of 800. Additionally, the accuracy of genomic prediction for Test-and-Shelf was analyzed when genomic prediction was applied on Pre-TC1 with an estimation data set from a previous year.

The prediction target consisted of 48 doubled haploid populations including 25 $F_1$-derived doubled haploid populations, 18 $F_2$-derived doubled haploid populations, two three-way- and three four-way crosses. The candidate set for the Pre-TC1 studies consisted of doubled haploid populations that were created two years prior to the creation of the populations of the prediction target, while the candidate set for the Test-and-Shelf study consisted of populations of the prediction target. To evaluate the informative value of hybrids from key inbreds, the six inbreds that were used most often in the prediction target were used to create hybrids from all possible two-way and four-way combinations of those inbreds, i.e., 15 $F_1$-derived doubled haploid populations and 15 four-way-doubled haploid populations. Each population in the candidate set had 80 hybrids.

The accuracy of genomic estimated breeding values on Pre-TC1, measured as correlation within population between the genomic estimated breeding value and the simulated true breeding value, was 0.02 higher for optimized estimation data sets compared to randomized estimation data sets. In addition, adding hybrids from four-way-crosses to the estimation data set increased the accuracy of genomic estimated breeding values by 4-6% with the optimized estimation data sets, but the accuracy was less for randomized estimation data sets.

The accuracy for Test-and-Shelf was 0.03 higher for optimized estimation data sets as compared to randomized estimation data sets, and the accuracy for randomized estimation data sets was 0.1-0.13 lower than OPT when Genomic Selection was applied on Pre-TC1. Including hybrids from four-way crosses into the candidate set increased the accuracy by 4-6%.

Example 5

Estimation Set Optimization for Inbred Populations in Soy

In current soy breeding programs, selection candidates come from populations created by crossing two inbreds and selfing of subsequent generations so that only chromosome segments of the two inbred gametes circulate in the population. $F_1$ hybrids are produced from the inbred cross, each containing a copy of the two parental gametes. These gametes are recombined through multiple meioses until a new set of selection candidates is created. These steps are then repeated using the selected lines for a new generation of inbred parents.

To use the optimization approach, linkage disequilibrium (LD) between markers on the genome has to be derived for each population. This was done here as follows. True and estimated breeding values of an individual j from population i, which built the theoretical foundation of the optimization approach, can be written as $g_{ij}=z_{ij}'\beta$ and $\hat{g}_{ij}=z_{ij}'\hat{\beta}$, respectively, where $z_{ij}$ is a vector of SNP genotypes. LD between markers is measured as the variance-covariance matrix of $z_{ij}$, $Var(z_{ij})$, which directly enters the optimization equations. Exact formulas are difficult to derive because of the multiple numbers of meioses and because of the inherent substructure within each single population. Therefore, $Var(z_{ij})$ was calculated empirically using Monte Carlo simulations of pedigrees and recombinations occurring during meioses. The variance-covariance matrix was estimated as $$\widehat{Var}(z_{ij}) = \frac{1}{N}\sum_{j=1}^{N} z_{ij} z_{ij}',$$

where N=20,000 individuals, which was larger than the number of SNP genotypes in $z_{ij}$, in order to generate a stable, well-conditioned, and possibly positive-definite variance-covariance matrix. Once this matrix was established, the optimization algorithm was run as with the corn examples.

The dataset for demonstrating advantages of optimization of estimation sets in soy breeding contained 19 populations with at least 168 individuals. These populations are larger than typical populations in corn breeding, resulting in higher potential for gains in accuracy with optimized estimation sets as compared to randomly assembled sets. For cross-validations, populations were randomly split into a prediction set and a candidate set of size 100. This was repeated 10 times. The optimization algorithm was applied to corresponding pairs of candidate and prediction sets containing individuals from the same population. The result is a ranking of the 100 individuals of the candidate set according to the highest expected increase of accuracy in the prediction set. To evaluate differences in accuracy between optimizations and a randomized approach at different estimation set sizes, subsets of sizes 5, 10, 15, 20, and 25 were generated from the final optimization result. For the optimization approach, the ranking was preserved, whereas for the randomized approach the subsets were randomly drawn from the candidate set. Estimation sets were used to estimate marker effects with BayesA, which were then used for prediction of GEBVs of individuals from the same population as in the estimation set.

Table 5 shows the correlation between observed and predicted phenotypes averaged over populations for different estimation set sizes generated both randomly and with the optimization approach. Except for an estimation set size of 5, optimizations resulted in larger correlations than the random design. Especially the estimation set size of 25 and 30 individuals showed a larger superiority than for corn breeding, most likely due to the larger population size.

TABLE 5

Correlation between observed and predicted phenotypes averaged over population according to estimation set size for optimized and random estimation sets

| Estimation set size | Optimized | Random | Optimized − Random |
| --- | --- | --- | --- |
| 5 | 0.086 | 0.083 | 0.00 |
| 10 | 0.145 | 0.133 | 0.01 |
| 15 | 0.180 | 0.162 | 0.02 |
| 20 | 0.207 | 0.185 | 0.02 |
| 25 | 0.229 | 0.199 | 0.03 |
| 30 | 0.240 | 0.212 | 0.03 |

What is claimed is:

1. A method for selecting individuals in a breeding program, said method comprising:

a. constructing an optimized estimation data set by:

(i) selecting a training candidate for phenotyping from a candidate set and placing the training candidate into the estimation data set, wherein genotypic information is available for the training candidate;

(ii) evaluating the accuracy of genomic estimated breeding values (GEBV) for future selection candidates coming from one or more populations in a prediction target, wherein a. when the prediction target has one population, said accuracy of genomic estimated breeding values is determined using the following formula:

$$\rho_{g_{ij}\hat{g}_{ij}} = \sqrt{\frac{4\sigma_\beta^2 tr\{G_i V_{yy}^{-1}\}}{N_i}}$$

b. when the prediction target has more than one population, said accuracy of genomic estimated breeding values is determined using the following formula:

$$\bar{\rho}_{g_{ij}\hat{g}_{ij}} = \frac{1}{N_I}\sum_{i=1}^{N_I}\rho_{g_{ij}\hat{g}_{ij}} \text{ or } \rho^{Iso}_{g_{ij}\hat{g}_{ij}} = \frac{1}{1-\delta}\sum_{i=1}^{N_I}\rho^{1-\delta}_{g_{ij}\hat{g}_{ij}};$$

or c. when the prediction target has a large number of populations, the following formula, wherein the accuracy of $\hat{g}_{ij}$ is replaced by the reliability of $\hat{g}_{ij}$, which is defined as $$r_{g_{ij}\hat{g}_{ij}} = \rho^2_{g_{ij}\hat{g}_{ij}} = \frac{4\sigma^2_\beta tr\{G_i V^{-1}_{yy}\}}{N_i};$$

wherein $g_{ij}$ is the true breeding value of selection candidate j from inbred population i;

$\hat{g}_{ij}$ is the estimated breeding value of selection candidate j from inbred population i;

$\sigma_\beta^2$ is the variance of SNP effects;

$G_i$ is a genomic relationship matrix weighted by the linkage disequilibrium of inbred population i;

$V_{yy}^{-1}$ is the inverse of the variance-covariance matrix of trait phenotypes of individuals in the estimation data set;

$N_i$ is the number of polymorphic SNPs of inbred population i; and $\delta$ is a risk aversion parameter;

(iii) moving the training candidate into the optimized estimation data set only if accuracy of genomic estimated breeding value of the future selection candidates coming from populations in the prediction target for that training candidate is higher than that of other training candidates in the candidate set; and (iv) continuing steps (i)-(iii) until an optimized estimation data set is generated;

b. growing one or more training candidates in the optimized estimation data set to create a population with increased GEBV accuracy for future selection candidates as compared GEBV accuracy using a randomized estimation data set;

c. phenotyping the training candidates in the optimized estimation data set;

d. genotyping breeding individuals at a plurality of markers;

e. obtaining genomic estimated breeding values for the breeding individuals utilizing phenotypes and genotypes of the training candidates in the optimized estimation data set;

f. selecting breeding individuals based on the genomic estimated breeding values; and g. crossing said selected breeding individuals to create an improved population of breeding individuals.

2. The method of claim 1, wherein said genotypic information for the candidate is obtained via genotyping or using Monte Carlo simulations.

3. The method of claim 1, wherein said breeding individuals are homozygous for a trait of interest or an allele.

4. The method of claim 1, wherein said breeding individuals are plants.

5. The method of claim 4, wherein said plants are selected from the group consisting of: maize, soybean, sunflower, sorghum, canola, wheat, alfalfa, cotton, rice, barley, millet, sugar cane and switchgrass.

6. The method of claim 1, wherein said breeding individuals are animals.

7. The method of claim 1, wherein said accuracy of genomic estimated breeding values is calculated using a mathematical formula that inputs marker information from candidates in the candidate set and marker information from parents of one or more populations making up the prediction target.

8. The method of claim 1, wherein said breeding individuals are inbreds or doubled haploids.

\* \* \* \* \*